United States Patent [19]
Kim et al.

[11] Patent Number: 5,959,166
[45] Date of Patent: *Sep. 28, 1999

[54] METHOD FOR CONCURRENTLY PRODUCING DIFFERENT HYDROFLUORO CARBONS

[75] Inventors: Hoon Sik Kim; Moon Jo Chung; Kun You Park; Young Soo Kwon, all of Seoul, Rep. of Korea

[73] Assignee: Korea Institute of Science and Technology, Seoul, Rep. of Korea

[ * ] Notice: This patent issued on a continued prosecution application filed under 37 CFR 1.53(d), and is subject to the twenty year patent term provisions of 35 U.S.C. 154(a)(2).

[21] Appl. No.: 08/966,093

[22] Filed: Nov. 7, 1997

Related U.S. Application Data

[63] Continuation of application No. 08/496,498, Jun. 29, 1995, abandoned.

[30] Foreign Application Priority Data

Jul. 4, 1994 [KR] Rep. of Korea .................. 94-15934

[51] Int. Cl.$^6$ ..................................................... C07C 17/08
[52] U.S. Cl. ............................................. 570/168; 570/169
[58] Field of Search ...................................... 570/169, 168

[56] References Cited

FOREIGN PATENT DOCUMENTS

| | | |
|---|---|---|
| 1196345 | 11/1985 | Canada . |
| 449 614 A2 | 10/1991 | European Pat. Off. . |
| 449 617 A2 | 10/1991 | European Pat. Off. . |
| 91-16657 | 11/1991 | Rep. of Korea . |
| 1000485 | 8/1965 | United Kingdom . |

*Primary Examiner*—Alan Siegel
*Attorney, Agent, or Firm*—Darby & Darby

[57] ABSTRACT

A method for concurrently producing different hydrofluoro carbons, comprising the reaction of halocarbon or hydrohalocarbon with hydrogen fluoride in a reaction system consisting of a series of at least two discrete reactors, in the presence of catalysts, said reactors each being provided with different reactant materials and differing in reaction conditions including the catalysts and/or reaction temperature, thereby flexibly controlling their production rates in accordance with fluctuations in their demand, and eliminating the risk of constructing large scale plants responsible for individual hydrofluorocarbons.

24 Claims, No Drawings

METHOD FOR CONCURRENTLY PRODUCING DIFFERENT HYDROFLUORO CARBONS

This is a continuation of application Ser. No. 08/496,498, filed Jun. 29, 1995 now abandoned.

BACKGROUND OF THE INVENTION

1. Field of the invention

The present invention relates, in general, to a method for producing different hydrofluorocarbons, simultaneously and, more particularly, to the use of a series of different reactors, each suitable for operating its own characteristic reaction process for the production of the individual hydrofluorocarbon.

2. Description of the Prior Art

Chlorofluorocarbon (hereinafter referred to as "CFC") compounds, extensively used for many purposes such as foaming agents, detergents, aerosol spraying agents and refrigerants, are destined to be prohibited from production and use in a few years in accordance with the internationally agreed protocol as they were proven to be a main factor destroying the ozone layer of the stratosphere. Accordingly, intensive research and study have been directed to the development of the substitutes that are not harmful to the ozone layer and functionally equal to CFC. As a result of extensive test for toxicity, stability and physicochemical performance, hydrofluorocarbon(HFC) compounds such as diflouromethane (HFC-32), trifluoromethane (HFC-23), 1,1-difluoroethane (HFC-152a), 1,1,1-trifluoroethane (HFC-143a), 1,1, 1,2-tetrafluoroethane (HFC-134a) and pentafluoroethane (HFC-125) were revealed to be potent substitutes for CFC. Of them, HFC-134a turned out to be able to replace dichlorodifluoromethane (CFC-12) and thus, it is already in commercial production. Yet the use of other compounds have not been sufficiently developed. At most there have been attempts to use a mixture of them as special refrigerants, for example, a mixture of HFC-134a, HFC-32 and HFC-143a, or of HFC-134a, HFC-32 and HFC-125 as a cooling agent.

Various methods were suggested to produce HFC compounds. For example, the methods disclosed in European Patent Nos. 0 449 614 A2 and 0 449 617 A2 and Korean Laid-Open Patent Publication No. 91-16657 are useful for the production of HFC compound, but only for one particular compound. The cited European patents record that HFC-134a can be produced from trichloroethylene (TCE) and hydrogenfluoride through a two-step reaction. It is written in the cited Korean patent that, when HFC-134a is produced from TCE and hydrogenfluoride through a two-step reaction, an addition of an inert gas to the reaction allows the reaction temperature to be controlled easily in addition to lowering the production of 1,1-difluoroethylene, a by-product.

Canadian Patent No. 1 196 345 discloses a method for the production of fluorinated carbons by which different products, such as HFC-134a, HFC-143a, HFC-125 and HCFC-133a, are produced from different reactants at different reaction temperatures in the presence of the same catalyst, composed of chromium fluoroxide. Likewise, U.S. Pat. No. 1,000,485 discloses that various kinds of hydrochlorofluoro carbons are produced from various reactants at appropriate reaction temperatures in the presence of aluminium fluoride catalyst.

Those methods disclosed in the above-cited patents, which produces one particular product from a particular reactant material, are quite different from the present invention in which at least two kinds of hydrofluoro carbons can be obtained, simultaneously.

Meanwhile, since an enormous capital investment is required for building a plant for the substitutes for CFC, it is not economical unless the production scale is significantly large. However, it seems likely that the construction of such a large plant is accompanied by great risk, when the large demand for the CFC substitutes is hard to be expected in the near future.

SUMMARY OF THE INVENTION

Accordingly, it is a principal object of the present invention to provide a method to produce different hydrofluorocarbons concurrently in the same reaction system, in response to a small demands of various products, thereby eliminating the risk of constructing individual large scale plants for individual HFC's.

It is another object of the present invention to provide a concurrent production method of different HFC's, capable of controlling their production rates in accordance with fluctuations in their demands.

In accordance with the present invention, the above objects could be accomplished by providing a method for the production of different HFC's, comprising the reaction of halocarbon or hydrohalocarbon with hydrogenfluoride in a reaction system consisting of a series of at least two discrete reactors, in the presence of catalysts, said reactors each being provided with different reactant materials and differing in reaction conditions including the catalysts and/or reaction temperature, whereby different HFC's can be produced concurrently.

DETAILED DESCRIPTION OF THE INVENTION

Turning now to a detailed description of the invention, which may be understood without reference to any drawing, one must first understand that HFC compounds, acknowledged as substitutes for CFC, are prepared from at least two kinds of halocarbons or hydrohalocarbons by replacing chlorines in the compounds with fluorines. The halocarbon or hydrohalocarbon used is selected from the group consisting of $CH_aX_b$ (X=Cl or F, a=1 or 2, b=4-a, and at least one Cl is contained), $CX_3CH_{a'}X_{b'}$, (X=Cl or F, a'=1, 2 or 3, b'=3-a', and at least one Cl is contained) and $C_2H_{a''}Cl_{b''}$(a"= 0, 1, 2 or 3, b"=4-a").

In more detail, HFC-32 and HFC-23 can be prepared by reacting dichloromethane and trichloromethane with hydrogen fluoride, respectively. 1-Chloro-1,1-difluoroethane (HCFC-142b) or 1,1-dichloro-1-fluoroethane (HCFC-141b) is selected as a reactant for HFC-143a, and chloroethylene for HFC-152a, 1-chloro-2,2,2-trifluoroethane (HCFC-133a) for HFC-134a and 1,1-dichloro-2,2, 2-trifluoroethane (HCFC-123) for HFC-125. The reactants, HCFC-133a and HCFC-123, can be obtained by reacting trichloroethylene (TCE) and perchloroethylene (PCE) with hydrogenfluoride, respectively.

It is preferred that the mole ratio of an organic reactant consisting of halocarbon and hydrohalocarbon to hydrogen fluoride is in the range of 1:2 to 1:50. When less amount of hydrogen fluoride is used, the replacement of the chlorine does not proceed effectively. On the other hand, when more amount of hydrogen fluoride is used, it is uneconomical because the concentration of the useful product in the product mixture becomes twoo low.

In accordance with a first embodiment of the present invention, there is provided a reaction system consisting of a series of at least two reactors wherein the reactant composition in a following reactor comprise all or a part of the products from the just preceding reactor as well as fresh reactant materials, halocarbons or hydrohalocarbons.

At least two HFC compounds selected from the group consisting of $CH_xF_y$ (x=1 or 2, y=4−x) and $CF_3CH_aF_b$ (a=1, 2 or 3 b=3−a) are obtained by the method of the present invention.

The catalysts in the present invention are aluminum, or chromium-based catalyst, as usual. Depending on reactions, different catalysts may be used in the unit reactors. Exemplary catalysts include chromium compounds such as chromium fluoride, chromium hydroxide, chromium oxide and chromium chloride, chromium fluoroxide, optionally in combination of magnesium fluoride or calcium fluoride and/or catalytically active metals such as cobalt and nickel.

As disclosed in the U.S patent and the Canadian patent cited, the catalysts and the reaction temperatures in the production of different HFC's could be different to each other. However, by virtue of the fact that, the above-explained reactions go through similar pathways to one another, a common step of chlorine-fluorine substitution reaction, a catalyst which is effective to one reaction is likely to be useful for the other reactions in most cases.

In addition, the present inventors carried out various experiments, from which it was revealed that, in the presence of chromium- or aluminum-based catalyst, HFC-32 and HFC-23 are prepared from dichloromethane and trichloromethane, respectively, and HFC-143a from HCFC-141b or HCFC-142b, HFC-152a from chlroloethylene, HFC-125 from HCFC-123 and HFC-134 from HCFC-133a.

Based on these facts, the present invention is distinguished by the characteristic method for producing at least two HFC compounds from at least two reactant materials, comprising the use of a series of at least two reactors, each employing different catalyst and/or operating at different reaction temperatures and provided with appropriate reactants according to the objective products, thereby overcoming the difference in optimal catalyst composition and optimal reaction conditions for each HFC product.

The present invention differs from the conventional techniques using a simple parallel of separate reactors in that, while each of the reactors in the parallel reaction system performs its own reaction with a provision of fresh reactants pertinent to the reaction, those reactors in the present series reaction system, each conducting its own characteristic reaction, may share reactants with each other. In more detail, a preceding reactor in the series reaction system takes up reactants pertinent to its own reaction, goes through the reaction and gives products to the next following reactor which is also provided with fresh reactants different from the preceding reactants as well as an additional portion of the same ones to the preceding reactants.

When the reaction temperature in the preceding reactor is lower than that in the next following one, the preceding organic reactant materials transferred into the next following reactor further experience the same reaction in the preceding one, giving rise to an increase in the conversion rate as well as a change in the selectivity. In contrast, when the reaction temperature in the preceding reactor is higher than that in the next following one, experiments showed that there is little or no change in the conversion rate and selectivity of the preceding reactants. In the latter case, it is preferred that the difference between the two reactors is about 20° C. provided that the same catalyst is used in the two reactors.

In two or more reactors which are interconnected in series, an exothermic reaction that produces more reaction heat is preferably carried out in the next following reactor because the products discharged from the preceding reactor act as diluents, and the reaction heat in the next reactor could be controlled easily.

Besides, the series combination of separate reactors allows the various products via different reaction steps to be produced concurrently with significant efficiency. For example, HFC-125 and HFC-32 can be produced concurrently in a series of two reactors. HFC-125 is efficiently prepared through two-step reaction in which PCE reacts with hydrogen fluoride at a temperature of 220 to 290° C. in the presence of an aluminium- or chromium-based catalyst to give a product mixture comprising a predominance of HCFC-123, which then also reacts with hydrogen fluoride but at a higher temperature, e.g. 300 to 380° C. in the presence of a chromium-based catalyst. Meanwhile, under the same reaction conditions as the production of HFC-125, that is, at a temperature of 300 to 380° C. in the presence of a chromium-based catalyst, HFC-32 can be efficiently obtained by reacting dichloromethane with hydrogen fluoride. These reactions are carried out in a series of two reactors, wherein a product mixture containing a predominance of HCFC-123 is prepared from PCE in the preceding reactor and all of the reaction products or the remainder after removing hydrogen chloride therefrom is provided along with dichloromethane to the next following reactor, so as to produce HCF-125 and HFC-32, concurrently and efficiently.

Alternatively, the order of the reactions may be reversed. That is, both HFC-125 and HFC-32 are produced in a preceding reactor which is provided with HCFC-123 and dichloromethane along with hydrogen fluoride at a temperature of 300 to 380° C. in the presence of a chromium-based catalyst, followed by further production of HFC-123 with a provision of PCE and the preceding reaction products in the next following reactor at 220 to 290° C. From the final product mixture, HFC-125, HFC-32 and hydrogen chloride are separated and the resulting remainder in which HFC-123 and hydrogen fluoride are predominant is recycled into the preceding reactor.

As in the above description, the reverse order, that is, the executing of a high temperature reaction ahead of a low temperature reaction results in mixing the high temperature products discharged from the preceding reactor with cold liquid PCE, so as to achieve the cooling of the products and the vaporization of the reactant material for the following reaction, simultaneously and efficiently. Accordingly, a significant advantage resulting from the performance of a higher temperature reaction in a preceding reactor and a lower temperature reaction in the next following reactor is an economy in energy. In this case, it was confirmed by experiments that HFC-125 and HFC-32 produced in the preceding reactor were kept stable in the following reactor, which is of lower temperature, without decomposition nor conversion into other materials.

Following is the concurrent production of HFC-134a and HFC-143a in two reactors which is connected to each other in series, another embodiment of the present invention.

To begin with, TCE reacts with hydrogen fluoride at a temperature 200 to 300° C. in the presence of chromium fluoroxide to give a product mixture rich in HCFC-133a. Thereafter, all of the product mixture or the remainder after removing hydrogen chloride is provided along with HCFC-141b to the next following reactor and subjected to reaction with hydrogen fluoride at a temperature of 340 to 400° C., so as to yield HFC-134a and HFC-143a, simultaneously.

The reaction of TCE with hydrogen fluoride produces not only HFC-134a but also HFC-143a, a by-product which degrades the conversion of HCFC-133a into HFC-134a.

However, when HFC-134a and HFC-143a are concurrently produced in accordance with the method of the present invention, HFC-143a prepared from HCFC-141b is present in such a concentration claose to a thermodynamic equilibrium, the production of HFC-143a from HCFC-133a, the side-reaction, is suppressed, which leads to an improvement in the conversions of HCFC-133a into HFC-134a.

Also, it is possible to reverse the order of those reactions responsible for the concurrent production of HFC-134a and HFC-143a, in accordance with the present invention. That is, both HFC-134a and HFC-143a are produced in the preceding reactor which is provided with HCFC-133a and HCFC-141b along with hydrogen fluoride at a temperature of 340 to 400° C., followed by production of HCFC-133a with a provision of the preceding reaction products along with TCE and hydrogen fluoride in the next following reactor at 200 to 300° C. From the final product mixture, HFC-134a, HFC-143a and hydrogen chloride are separated, and the resulting remainder in which HFC-123 and hydrogen fluoride are predominant is recycled into the preceding reactor.

Besides improving the efficiency of energy as mentioned in the previous embodiment, such reverse order can omit a step of removing hydrogen chloride from the product mixture in the preceding reactor, without degrading the overall efficiency of the reaction.

From the European patents cited supra, the present invention is well distinguished in many aspects on producing HFC-134a. For example, PCE, HCFC-123, HCFC-141b, HCFC-142b and dichloromethane or chloroethylene are simultaneously provided as reactant materials, in addition to TCE and hydrogen fluoride. As products, HFC-143a, HFC-125 and HFC-32 (or HFC-152a) as well as HFC-134a are yielded, concurrently. In effect, the present invention differs from the conventional techniques in the reactant composition provided for individual reaction steps, in the intrinsic reactions proceeding in each reaction step, and the resulting product composition of the reaction. Consequently, the present invention potentially has a significant advantage over the conventional techniques, including concurrent production of different HFC compounds along with HFC-134a without building additional plants.

For reaction pressure employed in the reactor system according to the present invention, the preferabla range is 4 to 10 kg/m$^2$.

A better understanding of the present method may be obtained in the following examples which are set forth to illustrate, and are not to be construed to limit, the present invention.

In the following examples, two 5 L monotube-type reactors were used and attended with accessory equipments including a vaporizer, a preheater and a distillation column. The series of reactors was installed inside of a cylindrical electrical furnace equipped with an automatic temperature controller. A catalyst weighing 4.5 to 5 kg was charged into the reactors. A metering pump was used to control the flow rate of reactant materials into the reactors. The preheater was located just before the first reactor, to provide hot gaseous materials to the first reactor, and its temperature was adjusted as the discharge temperature becomes equal to the set temperature at the inlet of the first reactor. A product mixture from the first reactor was provided to the second reactor after being mixed with fresh liquid reactant materials at the vaporizer. The vaporizer was adjusted in such a way that the temperature of the discharge therefrom might be equal to that at the inlet of the second reactor. For reaction pressure, a range of 7 to 10 kg/cm$^2$ was maintained in the first reactor and 4 to 6 kg/cm$^2$ in the second reactor.

EXAMPLE I

HCFC-123, HCFC-133a and hydrogen fluoride which had a flow rate of 3.0 g-mol/h, 7.0 g-mol/h and 100 g-mol/h, respectively, were mixed and provided through a preheater to the first reactor. It was charged with 5 kg of chromic fluoroxide and the temperature was kept at 380° C.

The mole composition of the organic products from the first reactor was given as follows:

| HCFC-133a | 50.4% | HCFC-124 | 1.5% |
|---|---|---|---|
| HFC-125 | 28.2% | HFC-143a | 0.4% |
| HFC-134a | 19.2% | HCFC-123 | 0.3% |

An analysis of these results revealed that the conversion of HCFC-123 and HCFC-133a were 99% and 28%, respectively and the selectivity to HFC-125 and HFC-134a were 95% and 98%, respectively.

The product mixture discharged from the first reactor was mixed with PCE having a flow rate of 5.5 g-mol/h and then, provided to the second reactor which was charged with 5 kg of a catalyst prepared by the fluorination of chromium oxide. The temperature in the second reactor was kept at 280° C.

The mole composition of the final organic products from the second reactor was given as follows:

| HCFC-133a | 32.5% | HCFC-124 | 6.3% |
|---|---|---|---|
| HFC-125 | 31.5% | PCE | 2.5% |
| HCFC-123 | 13.6% | HFC-143a | 0.2% |
| HFC-134a | 12.4% | Others | 1.0% |

An analysis of these results showed that the conversion of PCE in the second reactor was calculated as 93%.

It is believed that the reaction of HCFC-123 into HFC-125 and the reaction of HCFC-133a into HFC-134a take place predominantly in the first reactor whereas the reaction of PCE into HCFC-123, HCFC-124 and HFC-125 is predominant in the second reactor.

Hence, HFC-125 along with HFC-134a could be produced from PCE and HCFC-133a, according to the present invention.

EXAMPLE II

HCFC-133a, HCFC-142b and hydrogen fluoride which had a flow rate of 8.0 g-mol/h, 4.0 g-mol/h and 100 g-mol/h, respectively, were mixed and provided through a preheater to the first reactor. It was charged with 5 kg of a catalyst mixture of chromium fluoroxide and magnesium fluoride and the temperature was kept at 380° C.

The mole composition of the organic products discharged from the first reactor was given as follows:

| HCFC-133a | 48.0% |
|---|---|
| HFC-143a | 33.4% |
| HFC-134a | 18.3% |
| HFC-125 | 0.3% |

An analysis of these results revealed that the conversion of HCFC-133a and HFC-142b were 28% and near 100%, respectively and the selectivity into HFC-134a and HFC-143a were 98% and near 100%, respectively.

The product mixture from the first reactor was provided to the second reactor after mixing with PCE of a flow rate of 2.24 g-mol/h in the vaporizer. The second reactor was charged with 5 kg of the same catalyst as that of the first reactor. The temperature in the second reactor was kept at 270° C.

The mole composition of the final organic products from the secondreactor was given as follows:

| | |
|---|---|
| HCFC-133a | 56.1% |
| HFC-143a | 28.1% |
| HFC-134a | 15.4% |
| HFC-125 | 0.3% |
| TCE | 0.1% |

From these results, the conversion of PCE and the selectivity into HCFC-133a in the second reactor were calculated to 99.5% and near 100%, respectively.

It is believed that the reaction of HCFC-142b into HFC-143a and the reaction of HCFC-133a into HFC-134a take place predominantly in the first reactor, whereas the reaction of PCE into HCFC-133a is predominant in the second reactor.

From the final reaction products, hydrogen chloride was removed by distillation and HFC-143a and HFC-134a were separated. The consumed hydrogen fluoride and HCFC-142b were supplemented to the remainder and then the mixture was recycled as the reactant materials of the first reactor.

Hence, HFC-134a and HFC-143a can be, in sequence, produced from TCE and 142b, according to the present invention.

COMPARATIVE EXAMPLE I

HCFC-133a and hydrogen fluoride which had a flow rate of 10.0 g-mol/h and 100 g-mol/h, respectively, were mixed and provided through a preheater to the first reactor. It was charged with 5 kg of a catalyst mixture of chromium fluoroxide and magnesium fluoride and its temperature was kept at 380° C.

The mole composition of the organic products from first reactor is given as follows:

| | |
|---|---|
| HCFC-133a | 71.8% |
| HFC-134a | 27.2% |
| HFC-143a | 0.6% |
| HFC-125 | 0.4% |

From these results, the conversion of HCFC-133a and the selectivity into HFC-134a were calculated to 28% and near 96%, respectively.

The product mixture from the first reactor was provided to the second reactor after mixing with PCE of a flow rate of 2.82 g-mol/h in the vaporizer. The second reactor was charged with 5 kg of the same catalyst as that of the first reactor. The temperature of the second reactor was kept at 280° C.

The mole composition of the final organic products from the second reactor was given as follows:

| | |
|---|---|
| HCFC-133a | 77.9% |
| HFC-134a | 21.2% |
| HFC-143a | 0.5% |
| HFC-125 | 0.3% |
| TCE | 0.1% |

An analysis of this mole composition shows that the conversion rate of TCE and the selectivity into HCFC-133a in the second reactor are above 99.6% and near 100%, respectively.

From the final reaction products, hydrogen chloride was removed by distillation and HFC-134a was separated. The remainder was added with as much hydrogen fluoride as had been consumed for the reaction and then used as the reactant materials of the first reactor.

From the above results, it is believed that the reaction of HCFC-133a into HFC-134a occurs predominantly and HFC-143a and HFC-125 are produced from a side reaction in the first reactor, whereas the reaction of TCE into HCFC-133a is predominant but production of HFC-134a from HFC-134a is little in the second reactor.

The reaction of HCFC-133a into HFC-134a in Examples I and II are compared with that in Comparative Example I below. When the same catalysts are used for the same contact time at the same temperature in the first reactors, where the HFC-134a producing reaction is almost completed, the conversion of HCFC-133a becomes 28% in all the Examples As for the selectivity into HFC-134a, Examples I and II both show 98%, better than Comparative Example I, 96%. This improvement is believed to be attributed to the fact that HFC-125 and HFC-143a are rich in the products of Examples 1 and II which suppress the production of HFC-125 and HFC-143a by side-reactions along with the production of HFC-134a.

EXAMPLE III

HCFC-133a and hydrogen fluoride which had a flow rate of 10.0 g-mol/h and 25 g-mol/h, respectively, were mixed and provided through a preheater to the first reactor. It was charged with 5 kg of a catalyst mixture of chromium fluoroxide and magnesium fluoride and its temperature was kept at 360° C.

The mole composition of the organic products from the first reactor is given as follows:

| | |
|---|---|
| HCFC-133a | 75.8% |
| HFC-134a | 23.3% |
| HFC-143a | 0.6% |
| HFC-125 | 0.3% |

An analysis of this results reveals that the conversion of HCFC-133a and the selectivity into HFC-134a are 24% and 96%, respectively, in the first reactor.

The product mixture from the first reactor was mixed with TCE of a flow rate of 2.82 g-mol/h and dichloromethane of 3.0 g-mol/h and then provided through the vaporizer to the second reactor which was charged with 5 kg of the same catalyst as that of the first reactor. The temperature of the second reactor was maintained at 280° C.

The mole composition of the final organic products from the second reactor is given as follows:

| | | | |
|---|---|---|---|
| HCFC-133a | 64.9% | HFC-143a | 0.4% |
| HFC-32 | 18.1% | Dichloromethane | 0.3% |
| HFC-134a | 15.1% | HFC-125 | 0.2% |
| Others | 1.0% | | |

An analysis of these results showed that the conversion of TCE and dichloromethane were near 100% and 98%, respectively, and the selectivity into HCFC-133a and HFC-32 were near 100% and 95%, respectively, in the second reactor.

From the final reaction products, hydrogen chloride was removed taken off by distillation and HFC-134a was separated. HCFC-133a and hydrogen fluoride contained in the remainder were recycled. For this, the consumed hydrogen fluoride was supplemented.

Hence, HFC-32 and HCFC-134a could be, in sequence, produced from TCE and dichloromethane, according to the present invention.

EXAMPLE IV

HCFC-133a, HCFC-123 and hydrogen fluoride which had a flow rate of 5 g-mol/h, 2 g-mol/h and 100 g-mol/h, respectively, were mixed and provided through a preheater to the first reactor. It was charged with 5 kg of a catalyst mixture of chromium fluoroxide and magnesium fluoride and its inside temperature was kept at 370° C.

The mole composition of the organic products discharged from the first reactor was given as follows:

| HCFC-133a | 51.9% | HCFC-124 | 0.6% |
|---|---|---|---|
| HFC-125 | 27.9% | HFC-143a | 0.4% |
| HFC-134a | 19.1% | HCFC-123 | 0.3% |

An analysis of this mole composition reveled that the conversion of HCFC-133a and HCFC-123 were 27% and 99%, respectively and the selectivity into HFC-134a and HFC-125 both were 98%.

The product mixture from the first reactor was mixed with TCE having a flow rate of 1.37 g-mol/h and dichloromethane having 1.5 g-mol/h and then, provided through the vaporizer to the second reactor which was charged with 5 kg of the same catalyst as that of the first reactor. The temperature of the second reactor was maintained at 280° C.

The mole composition of the final organic products from the second reactor was given as follows:

| HCFC-133a | 50.5% | HCFC-124 | 0.4% |
|---|---|---|---|
| HFC-125 | 19.7% | Dichloromethane | 0.3% |
| HFC-32 | 14.4% | HFC-143a | 0.3% |
| HFC-134a | 13.6% | HCFC-123 | 0.2% |
| Others | 0.6% | | |

An analysis of these results showed that the conversion of TCE and dichloromethane were almost 100% and 99%, respectively and the selectivity into HCFC-133a and HFC-32 were almost 100% and 96%, respectively, in the second reactor.

From the above results, it was believed that the reaction of HCFC-133a into HFC-134a and the reaction of HCFC-123 into HFC-125 were predominant in the first reactor whereas the reaction of TCE into HCFC-133a and the reaction of dichloromethane into HFC-32 were predominant in the second reactor.

From the final reaction products, hydrogen chloride was removed by distillation and HFC-32, HFC-134a and HFC-125 were separated. HCFC-133a and hydrogen fluoride were isolated from the remainder and recycled into the first reactor. For this, the consumed hydrogen fluoride and HCFC-123 were supplemented.

Hence, HFC-32, HCFC-134a and HFC-125 could be concurrently produced from TCE and dichloromethane, according to the present invention.

EXAMPLE V

HCFC-123, trichloromethane and hydrogen fluoride which had a flow rate of 9.0 g-mol/h, 4.0 g-mol/h and 140 g-mol/h, respectively, were mixed and provided through the preheater to the first reactor. It was charged with 5 kg of a catalyst prepared by the fluorination of chromic oxide and its temperature was kept at 320° C.

The product mixture from the first reactor was mixed with HCFC-141b having a flow rate of 5 g-mol/h and then, provided through the vaporizer to the second reactor which was charged with 4.5 kg of the same catalyst as that of the first reactor. The temperature of the second reactor was maintained at 300° C.

The mole composition of the final organic products from the second reactor is given as follows:

| HFC-125 | 38.7% | HCFC-124 | 6.4% |
|---|---|---|---|
| HFC-143a | 26.1% | HCFC-123 | 4.5% |
| HFC-23 | 20.9% | HCFC-142b | 1.4% |
| Trichloromethane | 1.1% | HCFC-141b | 0.3% |
| Others | 0.6% | | |

An analysis of these results showed that the conversion of HCFC-123 and trichloromethane were 91% and 95%, respectively and the selectivity into HFC-125 and HFC-23 were 85% and 95%, respectively.

Hence, HCFC-125, HFC-23 and HCFC-143a could be concurrently produced from HCFC-123, trichloromethane and HCFC-141b, according to the present invention.

EXAMPLE VI

Dichloromethane and hydrogen fluoride which had a flow rate of 5.0 g-mol/h and 150 g-mol/h, respectively, were mixed and provided through the preheater to the first reactor. It was charged with 5 kg of a catalyst prepared by the fluorination of chromium oxide and its temperature was kept at 280° C.

The product mixture from the first reactor was mixed with HCFC-141b and chloroethylene, both having a flow rate of 5.0 g-mol/h, and then, provided through the vaporizer to the second reactor which was charged with 4.5 kg of a catalyst mixture of chromium fluoroxide and aluminum fluoride. The temperature inside the second reactor was maintained at 200° C.

The mole composition of the final organic products from the second reactor was given as follows:

| HFC-143a | 32.7% | Chloroethylene | 1.0% |
|---|---|---|---|
| HFC-32 | 31.7% | Dichloromethane | 0.7% |
| HFC-152a | 31.4% | HCFC-141b | 0.3% |
| HCFC-142b | 0.3% | Others | 1.9% |

An analysis of this mole composition showed that the conversion of dichloromethane, HFC-141b and chloroethylene were 98%, 99% and 97%, respectively and the selectivity into HFC-32, HFC-143a and HFC-152a were 97%, 99% and 97%, respectively.

Hence, HFC-32, HFC-143a and HFC-152a can be concurrently produced from dichloromethane, HCFC-141b and chloroethylene, according to the present invention.

Other features, advantages and embodiments of the invention disclosed herein will be readily apparent to those exercising ordinary skill after reading the foregoing disclosures. In this regard, while specific embodiments of the invention have been described in considerable detail, variations and modifications of these embodiments can be effected without departing from the spirit and scope of the invention as described and claimed.

What is claimed is:

1. A method for concurrently producing at least two different hydrofluorocarbon products, the method comprising:

reacting, at a first reaction temperature in a first discrete reactor, at least one first organic reactant with hydrogen fluoride in the presence of a first catalyst system to yield a first reaction composition;

reacting, at a second reaction temperature in a second discrete reactor, the first reaction composition and at least one second organic reactant with hydrogen fluoride in the presence of a second catalyst system to yield a second reaction composition; and recovering the at least two different hydrofluorocarbon products from the second reaction composition;

wherein the at least one first organic reactant and the at least one second organic reactant are different reactants, and the at least one first organic reactant and the at least one second organic reactant are each selected from the group consisting of halocarbons and hydrohalocarbons; and wherein the second discrete reactor is interconnected in series to the first discrete reactor such that each of the first discrete reactor and the second discrete reactor can share reactants with the other of the first discrete reactor and the second discrete reactor.

2. The method of claim 1 wherein one of the first catalyst system and the second catalyst system is a single first catalyst.

3. The method of claim 2 wherein the other of the first catalyst system and the second catalyst system is a single second catalyst.

4. The method of claim 2 wherein the first catalyst and the second catalyst are the same catalyst.

5. The method of claim 1 wherein the first catalyst system and the second catalyst system are the same catalyst system, and the first reaction temperature is different from the second reaction temperature.

6. The method of claim 1 wherein the first catalyst system is different from the second catalyst system, and the first reaction temperature is different from the second reaction temperature.

7. The method of claim 1 wherein the first catalyst system is different from the second catalyst system, and the first reaction temperature and the second reaction temperature are the same reaction temperature.

8. The method of claim 1 wherein the at least two different hydrofluorocarbon products are selected from the group consisting of $CH_xF_y$ (x=1 or 2 and y=4−x) and $CF_3CH_aF_b$ (a=1, 2 or 3 and b=3−a).

9. A method in accordance with claim 1, wherein said halocarbons and hydrohalocarbons are selected from the group consisting of $CH_aX_b$ (X=Cl or F, a=1 or 2, b=4−a, and at least one Cl is contained), $CX_3CH_{a'}X_{b'}$ (X=Cl or F, a'=1, 2 or 3, b'=3−a', and at least one Cl is contained) and $C_2H_{a''}Cl_{b''}$ (a''=0, 1, 2 or 3, b''=4−a'').

10. A method in accordance with claim 1 wherein said first discrete reactor yields reaction products, and all or a part of said reaction products are provided to said second discrete reactor in addition to said halocarbons and hydrohalocarbons.

11. A method in accordance with claim 1 wherein said hydrofluorocarbon products are at least two compounds selected from the group consisting of $CH_xF_y$ (x=1 or 2 and y=4−x) and $CF_3CH_aF_b$ (a=1, 2 or 3 and b=3−a).

12. A method in accordance with claim 1, wherein one of said first catalyst system and said second catalyst system comprises at least one catalyst selected from the group consisting of chromium oxide, chromium fluoride and chromium fluoroxide in combination with at least one catalyst selected from the group consisting of magnesium fluoride, aluminum fluoride and aluminum oxide.

13. A method in accordance with claim 1, wherein a molar ratio of total organic reactant materials to hydrogen fluoride is 1:2 to 1:50.

14. A method in accordance with claim 1, wherein said second discrete reactor yields unreacted reactant materials and intermediate products, and said unreacted reactant materials and intermediate products are provided to said first discrete reactor.

15. A method in accordance with claim 1, wherein said reaction temperature is in the range of 200° C. to 400° C.

16. A method in accordance with claim 5, wherein said first reaction temperature differs from said second reaction temperature by 20° C. or more.

17. A method in accordance with claim 1, wherein the reaction is carried out at a pressure of 4 to 10 kg/cm².

18. A method in accordance with claim 1, wherein said catalyst is selected from the group consisting of chromium oxide, chromium fluoride and chromium fluoroxide.

19. A method for concurrently producing at least two different hydrofluorocarbon products, the method comprising:

reacting, at a first reaction temperature in a first one of at least two discrete reactors, at least one first organic reactant with hydrogen fluoride in the presence of a first catalyst system to yield a first reaction composition;

reacting, at a second reaction temperature in a second one of said at least two discrete reactors, the first reaction composition and at least one second organic reactant with hydrogen fluoride in the presence of a second catalyst system to yield a second reaction composition; and recovering the at least two different hydrofluorocarbon products from the second reaction composition;

wherein the at least one first organic reactant and the at least one second organic reactant are different reactants, and the at least one first organic reactant and the at least one second organic reactant are each selected from the group consisting of halocarbons and hydrohalocarbons; and wherein the at least two discrete reactors are interconnected in series such that each of the at least two discrete reactors can share reactants with the another of the at least two discrete reactors.

20. The method of claim 19 wherein the first catalyst system and the second catalyst system are the same catalyst system, and the first reaction temperature is different from the second reaction temperature.

21. The method of claim 19 wherein the first catalyst system is different from the second catalyst system, and the first reaction temperature is different from the second reaction temperature.

22. The method of claim 19 wherein the first catalyst system is different from the second catalyst system, and the first reaction temperature and the second reaction temperature are the same reaction temperature.

23. The method of claim 19 wherein the at least two different hydrofluorocarbon products are selected from the group consisting of $CH_xF_y$ (x=1 or 2 and y=4−x) and $CF_3CH_aF_b$ (a=1, 2 or 3 and b=3−a).

24. A method in accordance with claim 1, wherein the first reaction temperature and the second reaction temperature are the same temperature.

* * * * *